US011089941B2

(12) United States Patent
Pereira et al.

(10) Patent No.: US 11,089,941 B2
(45) Date of Patent: Aug. 17, 2021

(54) MEDICAL SYSTEM FOR IDENTIFYING MATERIAL TO BE REMOVED FROM A PATIENT AND RELATED METHODS

(71) Applicant: Boston Scientific Scimed, Inc., Maple Grove, MN (US)

(72) Inventors: Peter J. Pereira, Mendon, MA (US); Chad Schneider, Owings Mills, MD (US); Brandon W. Craft, Edgewater, MD (US); Kimberly Degraaf, Holden, MA (US); Jozef Slanda, Milford, MA (US); James M. Goddard, Pepperell, MA (US); Christopher P. Gauvin, South Grafton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 491 days.

(21) Appl. No.: 15/969,967

(22) Filed: May 3, 2018

(65) Prior Publication Data

US 2018/0317743 A1    Nov. 8, 2018

Related U.S. Application Data

(60) Provisional application No. 62/501,466, filed on May 4, 2017.

(51) Int. Cl.
*A61B 1/00* (2006.01)
*G06T 7/00* (2017.01)
(Continued)

(52) U.S. Cl.
CPC ........ *A61B 1/00009* (2013.01); *A61B 1/0005* (2013.01); *A61B 1/0051* (2013.01);
(Continued)

(58) Field of Classification Search
CPC ..... A61B 1/00009; A61B 34/10; A61B 18/26; A61B 1/0051; A61B 1/0005;
(Continued)

(56) References Cited

U.S. PATENT DOCUMENTS 10,292,620 B1 *  5/2019  Choi ........................ A61B 5/00
10,368,820 B2 *  8/2019  Pereira ................ A61B 5/1076
(Continued)

FOREIGN PATENT DOCUMENTS

| EP | 2422736 A2 | 2/2012 |
|---|---|---|
| WO | WO 2014/139021 A1 | 9/2014 |
| WO | WO 2016/201341 A1 | 12/2016 |

OTHER PUBLICATIONS

International Search Report and Written Opinion for corresponding International Application No. PCT/US2018/030789, dated Aug. 20, 2018 (11 pages).

*Primary Examiner* — Amanda Lauritzen Moher
(74) *Attorney, Agent, or Firm* — Bookoff McAndrews, PLLC

(57) ABSTRACT

A method for identifying material to be removed from a patient may use an imaging device, a display, a control unit, and an insertion device. The method may include obtaining a first set of image data from the imaging device, sending the first set of image data to the control unit from the imaging device, and analyzing the first set of image data based on at least one of a darkness, a contrast, or a saturation. The method may include generating a coded image identifying the material to be removed from the patient to be displayed on the display. The method may further include displaying the coded image on a first screen of the display, and indicating the material to be removed with the insertion device based on the displayed coded image.

20 Claims, 6 Drawing Sheets

(51) Int. Cl.
 *A61B 18/26*    (2006.01)
 *A61B 1/005*    (2006.01)
 *A61B 6/00*     (2006.01)
 *A61B 17/221*    (2006.01)
 *A61B 1/307*    (2006.01)
 *A61B 34/10*    (2016.01)
 *A61B 18/00*    (2006.01)
 *A61B 18/22*    (2006.01)

(52) U.S. Cl.
 CPC ............ *A61B 1/307* (2013.01); *A61B 6/4452* (2013.01); *A61B 6/481* (2013.01); *A61B 6/5205* (2013.01); *A61B 6/5235* (2013.01); *A61B 17/221* (2013.01); *A61B 18/26* (2013.01); *A61B 34/10* (2016.02); *G06T 7/0012* (2013.01); *G06T 7/0014* (2013.01); *A61B 2017/2215* (2013.01); *A61B 2018/00511* (2013.01); *A61B 2018/00642* (2013.01); *A61B 2018/2238* (2013.01); *A61B 2034/107* (2016.02)

(58) Field of Classification Search
 CPC ..... A61B 6/4452; A61B 6/481; A61B 6/5235; A61B 6/5205; A61B 17/221; A61B 1/307; A61B 2034/107; A61B 2018/00642; A61B 2018/2238; A61B 2018/00511; A61B 2017/2215; G06T 7/0012; G06T 7/0014
 See application file for complete search history.

(56) References Cited

U.S. PATENT DOCUMENTS

| | | | | |
|---|---|---|---|---|
| 2003/0095697 | A1* | 5/2003 | Wood | A61B 6/037 382/131 |
| 2004/0024311 | A1* | 2/2004 | Quaid, III | A61B 34/10 600/428 |
| 2007/0249933 | A1* | 10/2007 | Krauss | G06T 7/97 600/425 |
| 2007/0260214 | A1* | 11/2007 | Mikkaichi | A61B 1/00135 604/500 |
| 2011/0201932 | A1 | 8/2011 | Duric et al. | |
| 2012/0232375 | A1* | 9/2012 | Zebaze | A61B 6/032 600/407 |
| 2014/0185907 | A1* | 7/2014 | Chiba | A61B 1/00009 382/134 |
| 2015/0196193 | A1* | 7/2015 | Kienzle | A61B 1/00103 600/109 |
| 2015/0313444 | A1* | 11/2015 | Wolf | A61B 1/00006 600/103 |
| 2015/0366571 | A1* | 12/2015 | Navve | A61B 5/201 606/128 |
| 2017/0193160 | A1* | 7/2017 | Long | A61B 34/10 |

* cited by examiner

MEDICAL SYSTEM FOR IDENTIFYING MATERIAL TO BE REMOVED FROM A PATIENT AND RELATED METHODS

CROSS-REFERENCE TO RELATED APPLICATIONS

This patent application claims the benefit of priority under 35 U.S.C. § 119 to U.S. Provisional Patent Application No. 62/501,466, filed May 4, 2017, which is herein incorporated by reference in its entirety.

TECHNICAL FIELD

Various aspects of the present disclosure relate generally to systems and methods useful in planning and/or performing medical procedures.

BACKGROUND

Substantial progress has been made towards increasing the effectiveness of medical treatment while reducing trauma and risks to the patient. Many procedures that once required open surgery now may be done with less invasive techniques, thus providing for less recovery time and risks of infection for the patient. Certain procedures requiring biopsy, electro-stimulation, tissue ablation, or removal of native or foreign bodies may be performed through minimally-invasive surgery.

In the field of urology, for example, renal calculi or kidney stones can accumulate in the urinary tract and become lodged in the kidney. Kidney stones are deposits of materials from the urine, typically minerals and acid salts. While smaller stones may pass from the body naturally, larger stones can require surgical intervention for removal. While open surgery was once the standard treatment for the removal of stones, other less invasive techniques, such as ureteroscopy and percutaneous nephrolithotomy/nephrolithotripsy (PCNL), have emerged as safer, effective alternatives. Additionally, advances in imaging technology have improved a medical professional's ability to identify and locate stones before and during procedures. Nevertheless, medical professionals still must analyze images to determine the location of stones and whether any stones are present. Moreover, the images are often in grayscale, blurry, and otherwise difficult to evaluate, making the medical professional's task of discerning the presence of any stones challenging.

The systems, devices, and methods of the current disclosure may rectify some of the deficiencies described above, and/or address other aspects of the prior art.

SUMMARY

Examples of the present disclosure relate to, among other things, medical systems and methods. Each of the examples disclosed herein may include one or more of the features described in connection with any of the other disclosed examples.

In one example, the present disclosure includes, a system for identifying material to be removed from a patient comprising an imaging device configured to obtain image data, a display configured to display images, an insertion device, and a control unit. The control unit may be configured to receive a first set of image data from the imaging device, analyze the first set of image data based on at least one of a darkness, a contrast, or a saturation, and generate a coded image identifying the material to be removed from the patient to be displayed on the display.

The system may further include one or more of the following features. The insertion device may include a deflectable delivery shaft having at least one lumen extending through the delivery shaft, and the delivery shaft may include at least a camera and a light source positioned at a distal end of the delivery shaft. The display may include at least two screens, and a first screen may display the coded image and a second screen may display images from the camera. The system may further include at least one of a retrieval device or a laser source. The control unit may be further configured to control the imaging device or the display. The control unit may include a processing unit and a memory unit. The control unit may be configured to signal the imaging device to obtain a second set of image data, and the control unit may be further configured to compare the second set of image data with the coded image generated based on the first set of image data. Based on the comparison of the second set of image data with the coded image generated based on the first set of image data, the control unit may be further configured to indicate progress during a material removal procedure. Based on the comparison of the second set of image data with the coded image generated based on the first set of image data, the control unit may be further configured to indicate whether a material removal procedure is complete.

The obtained image data may be grayscale or monochrome, and the coded image may identify the material to be removed from the patient with a different color, pattern, or shape than an area that is free of the material to be removed. The identification of material to be removed from the patient in the coded image may further be based on at least one of size, density, and location. The coded image may indicate the location of the material relative to an organ of the patient. The coded image may indicate the size of the material and whether the material may be removed from the patient with a retrieval device. The imaging device may be a rotatable C-arm X-ray machine including an X-ray tube and an X-ray detector configured to be positioned on opposing sides of the patient. The control unit may be integrally incorporated within a handle of the insertion device.

In another example, a method for identifying material to be removed from a patient using an imaging device, a display, a control unit, and an insertion device may include obtaining a first set of image data from the imaging device, sending the first set of image data to the control unit from the imaging device, analyzing the first set of image data based on at least one of a darkness, a contrast, or a saturation, generating a coded image identifying the material to be removed from the patient to be displayed on the display, displaying the coded image on a first screen of the display, and indicating the material to be removed with the insertion device based on the displayed coded image.

The method may further include one or more of the following features. The method may further include removing at least a portion of the material from the patient with the insertion device, and removing the material from the patient may include deflecting a delivery shaft of the insertion device, viewing an interior organ of the patient with at least a camera and a light source positioned at a distal end of the delivery shaft, and displaying images obtained from the camera on a second screen of the display. The method may further include obtaining a second set of image data from the imaging device and comparing the second set of image data with the coded image generated based on the first set of image data. Based on the comparison of the second set of image data with the generated coded image and the first set of image data, the method may include indicating progress of a material removal procedure. The obtained image data may be grayscale or monochrome, and the method may further include identifying the material to be removed from the patient with a different color, pattern, or shape than an area that is free of the material to be removed.

The method may further include indicating the location of the material relative to an organ of the patient, identifying the material to be removed from the patient based on density, and indicating the size of the material and whether the material may be removed from the patient with a retrieval device. Obtaining the first set of image data from the imaging device may include using a rotatable C-arm X-ray machine including an X-ray tube and an X-ray detector configured to be positioned on opposing sides of the patient, and the control unit may be integrally incorporated within a handle of the insertion device.

In another example, a system for identifying material to be removed from a patient may include an imaging device configured to obtain image data, a display configured to display images, an insertion device, and a control unit. The control unit may be configured to receive a first set of image data from the imaging device, analyze the first set of image data based on at least one of a darkness, a contrast, or a saturation, and generate a coded image identifying the material to be removed from the patient to be displayed on the display.

The system may further include one or more of the following features. The insertion device may include a deflectable delivery shaft having at least one lumen extending through the delivery shaft. The delivery shaft may include at least a camera and a light source positioned at a distal end of the delivery shaft. The display may include at least two screens, and a first screen may display the coded image and a second screen may display images from the camera. The control unit may include a processing unit and a memory unit. The control unit may be configured to signal the imaging device to obtain a second set of image data, and the control unit may be further configured to compare the second set of image data with the coded image generated based on the first set of image data. Based on the comparison of the second set of image data with the coded image generated based on the first set of image data, the control unit may be further configured to indicate progress during a material removal procedure.

The obtained image data may be grayscale or monochrome, and the coded image may identify the material to be removed from the patient with a different color, pattern, or shape than an area that is free of the material to be removed. The coded image may indicate the location of the material relative to an organ of the patient, identify the material to be removed from the patient based on density, and indicate the size of the material and whether the material may be removed from the patient with a retrieval device. The imaging device may be a rotatable C-arm X-ray machine including an X-ray tube and an X-ray detector configured to be positioned on opposing sides of the patient, and the control unit may be is integrally incorporated within a handle of the insertion device.

In another example, a non-transitory computer-readable medium for identifying material to be removed from a patient may include instructions stored thereon, that when executed on a processor, perform the steps of receiving a first set of image data, analyzing the first set of image data based on at least one of a darkness, a contrast, or a saturation, and generating a coded image identifying the material to be removed from the patient displayable on a display, and sending the coded image to the display.

The non-transitory computer-readable medium may further include one or more of the following features. The non-transitory computer-readable medium may further include instructions, that when executed on a processor, further perform the step of displaying images obtained from a camera on a second display. The non-transitory computer-readable medium may further include instructions, that when executed on a processor, further perform the step of comparing a second set of image data with the coded image generated based on the first set of image data. The non-transitory computer-readable medium may further include instructions, that when executed on a processor, further include the step of, based on the comparison of the second set of image data with the generated coded image and the first set of image data, indicating progress of a material removal procedure. The step of generating the coded image identifying the material to be removed from the patient may include indicating the location of the material relative to an organ of the patient, identifying the material to be removed from the patient with a different color, pattern, or shape than an area that is free of the material to be removed, and indicating the size and/or density of the material and whether the material may be removed from the patient with a retrieval device. The step of receiving the first set of image data may include receiving image data from a rotatable C-arm X-ray machine including an X-ray tube and an X-ray detector configured to be positioned on opposing sides of the patient, and the step of analyzing the first set of image data may be performed by a processing unit integrally incorporated within a handle of an insertion device.

Both the foregoing general description and the following detailed description are exemplary and explanatory only and are not restrictive of the features, as claimed. As used herein, the terms "comprises," "comprising," or other variations thereof, are intended to cover a non-exclusive inclusion such that a process, method, article, or apparatus that comprises a list of elements does not include only those elements, but may include other elements not expressly listed or inherent to such a process, method, article, or apparatus. Additionally, the term "exemplary" is used herein in the sense of "example," rather than "ideal." As used herein, the terms "about," "substantially," and "approximately," indicate a range of values within +/−5% of a stated value.

BRIEF DESCRIPTION OF THE FIGURES

The accompanying drawings, which are incorporated in and constitute a part of this specification, illustrate various exemplary embodiments and together with the description, serve to explain the principles of the disclosure.

DETAILED DESCRIPTION

Examples of the present disclosure include systems and methods to facilitate, and improve the efficacy and safety of minimally-invasive surgeries. For example, aspects of the present disclosure may provide a user (e.g., a physician, medical technician, or other medical service provider) with the ability to more easily identify and, thus, remove kidney stones or other material from a patient's kidney or other organ. In some embodiments, for example, the present disclosure may be used in planning and/or performing a flexible ureteroscope procedure, with or without laser lithotripsy.

Reference will now be made in detail to examples of the present disclosure described above and illustrated in the accompanying drawings. Wherever possible, the same reference numbers will be used throughout the drawings to refer to the same or like parts.

The terms "proximal" and "distal" are used herein to refer to the relative positions of the components of an exemplary medical device or insertion device. When used herein, "proximal" refers to a position relatively closer to the exterior of the body or closer to an operator using the medical device or insertion device. In contrast, "distal" refers to a position relatively further away from the operator using the medical device or insertion device, or closer to the interior of the body.

Figure 1:
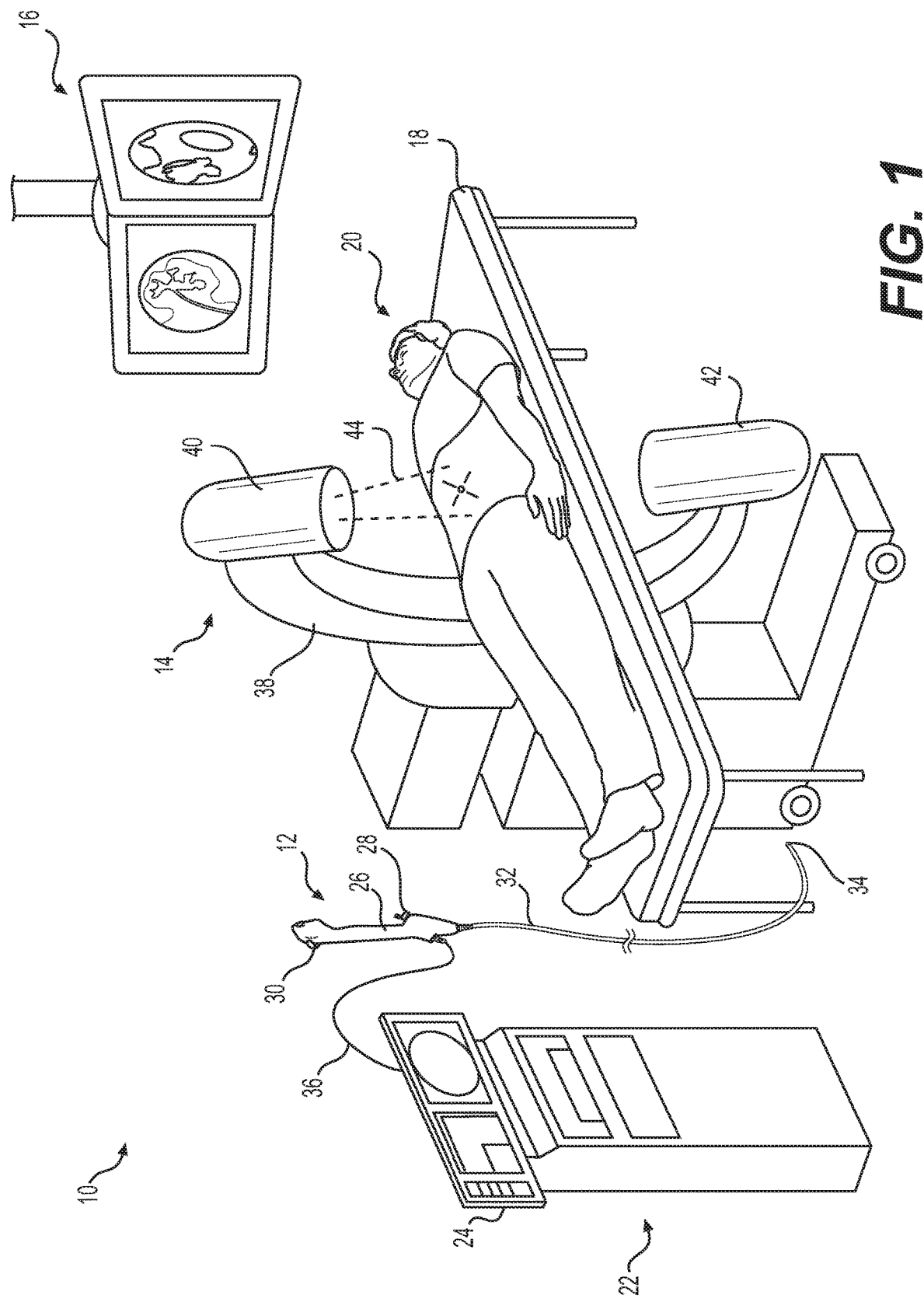
FIG. 1 illustrates a medical system, according to aspects of the present disclosure.

FIG. 1 illustrates a medical system 10 that includes a medical device 12, an imaging device 14, a display 16, and a patient support 18 for a patient 20. Medical device 14 may be wire connected (as shown), wirelessly connected, or otherwise coupled to a control unit 22. The imaging device 14 and/or the display 16 may also be wire connected, wirelessly connected, or otherwise coupled to control unit 22. Images and other patient information may be displayed on display 16 and/or a monitor 24 coupled to control unit 22.

As shown in FIG. 1, medical device 12 may be an insertion device such as, for example, a ureteroscope (e.g., LithoVue' Single-Use Digital Flexible Ureteroscope by Boston Scientific Corp.). Medical device 12 may include a handle 26 with at least one port 28 and a deflection lever 30. Port 28 may be threaded and may include a T-connector as shown in FIG. 1, a Y-connector, or another appropriate connector. Medical device 12 may also include a delivery shaft 32 terminating distally in a distal opening 34. The delivery shaft 32 may include a plurality of lumens, and the at least one port 28 may connect to a proximal end of the delivery shaft 32 through a lumen (not shown) in handle 26.

Various instruments or devices may be inserted through port 28 to be delivered to and/or out of distal opening 34 of delivery shaft 32, such as, for example, an energy device, such as a laser device for lithotripsy, and/or a retrieval basket. The distal end of delivery shaft 32 may be manipulated by action on the deflection lever 30. Handle 26 may also be connected to display 16 and/or control unit 22 via a communication and/or power conduit 36. For example, though not shown, medical device 12 may include an integral camera and/or light at the distal end of delivery shaft 32 that is/are connected to display 16 and/or monitor 24 of control unit 22 via the communication and power conduit 36. With medical device 12 positioned within patient 20, for example, through the patient's urethra to a patient's kidney, a retrieval device (not shown) may be inserted through port 28 and delivery shaft 32 and, using the integral camera and/or light and deflection lever 30, a user may manipulate the distal end of delivery shaft 32 and extend the retrieval device to retrieve and remove material such as, for example, a kidney stone, with or without using laser lithotripsy.

Imaging device 14 may be any medical imaging device used to collect patient data. For example, imaging device 14 may include an X-ray, Magnetic Resonance Imaging, Computerized Tomography Scan, rotational angiography, ultrasound, or another appropriate internal imaging device. For some imaging procedures, a contrast agent may be used to assist in identifying anatomical features in the images. For example, a contrast agent may be introduced into the patient (e.g., iodine, barium, or another appropriate contrast agent may be introduced via the patient's urinary tract via the ureter) prior to imaging to assist in visualization of the kidneys and urinary system.

In one example, imaging device 14 is a mobile C-arm device useful for collecting X-ray images of the patient 20 in preparation for and/or during a ureteroscopic procedure, according to some aspects of the present disclosure. As shown, the "C-arm" 38 of the imaging device 14 includes an X-ray tube 40 aligned with a detector 42 positioned on the opposite side of the patient 20. The C-arm 38 may be rotatable relative to the patient 20 in one or more planes (e.g., about an axis parallel and/or an axis perpendicular to the patient 20) to allow for the collection of images in different orientations, without moving the patient 20. The images may be displayed and analyzed in real time on a monitor or display, for example, monitor 24 and/or display 16. The images may also be stored locally or remotely for later viewing and analysis. For example, as discussed in more detail below, the C-arm device 38 may be used to collect patient images before a ureteroscopic procedure to locate and identify any stones or material to be removed. The user may consult the images for guidance on proper insertion and positioning of the ureteroscope and other instruments during the procedure. The C-arm device 38 may also be used during a ureteroscopic procedure to collect images of the stones or material relative to an inserted ureteroscope within, for example, a patient's kidney. The C-arm device 38 may also be used after a ureteroscopic procedure to determine whether all of the stones or material have been removed.

The mobile C-arm device 38 may include a light source to identify a specific target or region of a patient, such as an intended incision or insertion site. For example, the C-arm 38 may include a light source coupled to or incorporated into the X-ray tube 40, wherein the light source may be used to direct light on a pre-determined imaging location. FIG. 1 illustrates light 44 focused on the midsection of the patient 20 in the form of an "X" or crosshairs to indicate the intended imaging location. The direction, orientation, intensity, and/or shape of the light generated by the light source may be controlled via user input at the control unit 22 and/or by instructions received over a wireless connection from any appropriate user interface device.

Display 16 may be at least a dual screen display. In one example, one of the screens may display an image or images currently or previously obtained by imaging device 14. The other screen may display an image or video obtained by the camera at the distal end of delivery shaft 32. Alternatively, one screen of display 16 may display a previously obtained image from imaging device 14, and the other screen of display 16 may display a more recently obtained image from imaging device 14. Furthermore, one screen of display 16 may display an image or images obtained by an additional imaging device, or display other electronic medical record information, and another screen of display 16 may display an image or images obtained by imaging device 14 and/or an image or video obtained by the camera at the distal end of delivery shaft 32.

Patient support 18 may be a surgical stretcher, gurney, hospital bed, or surgical bed. Patient support 18 may be an urological surgical bed. Patient support 18 allows the imaging device 14 to capture internal images of the patient 20, and does not interfere with the ability of imaging device 14 to capture the images. Patient support 18 may also be adjustable and movable in order to better position the patient 20 while obtaining imaging and/or while performing the procedure.

Control unit 22 may be wired or wirelessly connected to medical device 12, imaging device 14, and/or display 16. A user may use control unit 22 and monitor 24 to initiate imaging and/or analysis and to otherwise control imaging device 14 and display 16. Control unit 22 may include one or more memory and/or processing units. The memory and/or processing units may include installed software or applications that may be preprogrammed or downloaded to be stored within the control unit 22 and/or the medical device 12. Additionally or alternatively, medical device 12 may include memory and/or processing units, and medical device 12 and control unit 22 may communicate, wired or wirelessly, with respect to memory and processing of patient data and obtained image data. As will be discussed in more detail below, the software or applications may manipulate, process, and interpret received images from imaging device 14 to identify the presence, location, and characteristics of a kidney stone or other material. Moreover, control unit 22 or medical device 12 may compare received images to previously received and analyzed images. For example, the user may employ control unit 22 or medical device 12 to process images from imaging device 14 to identify the presence of a stone and to determine the dimensions, density, composition, location, orientation, and/or position of the stone(s) relative to the kidney and the surrounding anatomy.

Figure 2:
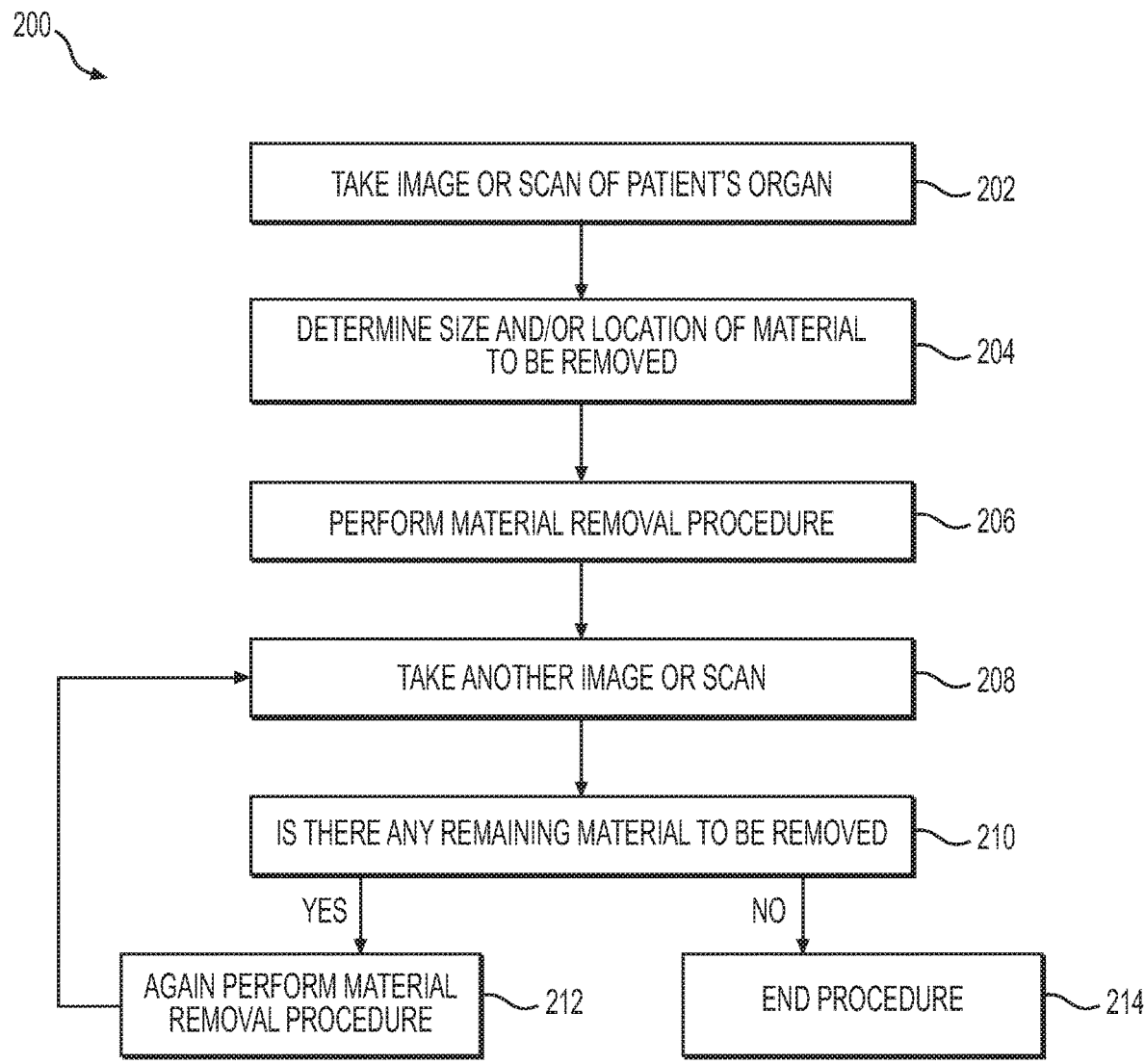
FIG. 2 is a flow diagram of an exemplary method for imaging and removing material from a patient's organ, according to aspects of the present disclosure.

FIG. 2 illustrates an exemplary method 200 for imaging and removing material from a patient's kidney, according to aspects of the present disclosure. In particular, the method 200 shown in FIG. 2 may help to ensure that a user removes the entirety of the kidney stones or other material from the patient 20.

As shown, in step 202, a user may first take an image or scan, using imaging device 14, of a patient's organ, such as, for example, kidney, and determine the size, location, and/or burden of the stone or material to be removed. Step 202 may include introducing a contrast agent in the patient in order to improve and/or enhance the clarity of the image or scan. Based on the image or scan, in step 204, the user, with the aid of the control unit 22, monitor 24, and display 16, may determine the size, location, and/or burden of the stone or material to be removed. For example, control unit 22 may combine the sizes of multiple stones or materials and determine an area or volume of stone or material occupying space in the patient's kidney. Then, in step 206, the user may perform the material removal procedure. As discussed above, step 206 may include inserting medical device 12 into patient 20, for example, through the patient's urethra into the kidney, and using an energy source and/or a retrieval device to break up and/or remove the kidney stones or other material.

Step 208 then includes taking another image or scan of the patient's organ. Based on this image or scan, in step 210, the user, again using the control unit 22, monitor 24, and display 16, may determine whether there is any remaining kidney stone or other material to be removed. If there is a kidney stone or other material to be removed remaining in the patient's organ, in step 212, the user may again perform the material removal procedure. The user may then repeat steps 208 and 210 as many times as necessary to take an image or scan of the organ and determine whether the material has been removed. If, however, there is not a kidney stone or other material to be removed remaining in the patient's organ, then the user may end the procedure in step 214. Ending the procedure may include removing the medical device 12 from the patient 20.

Figure 3:
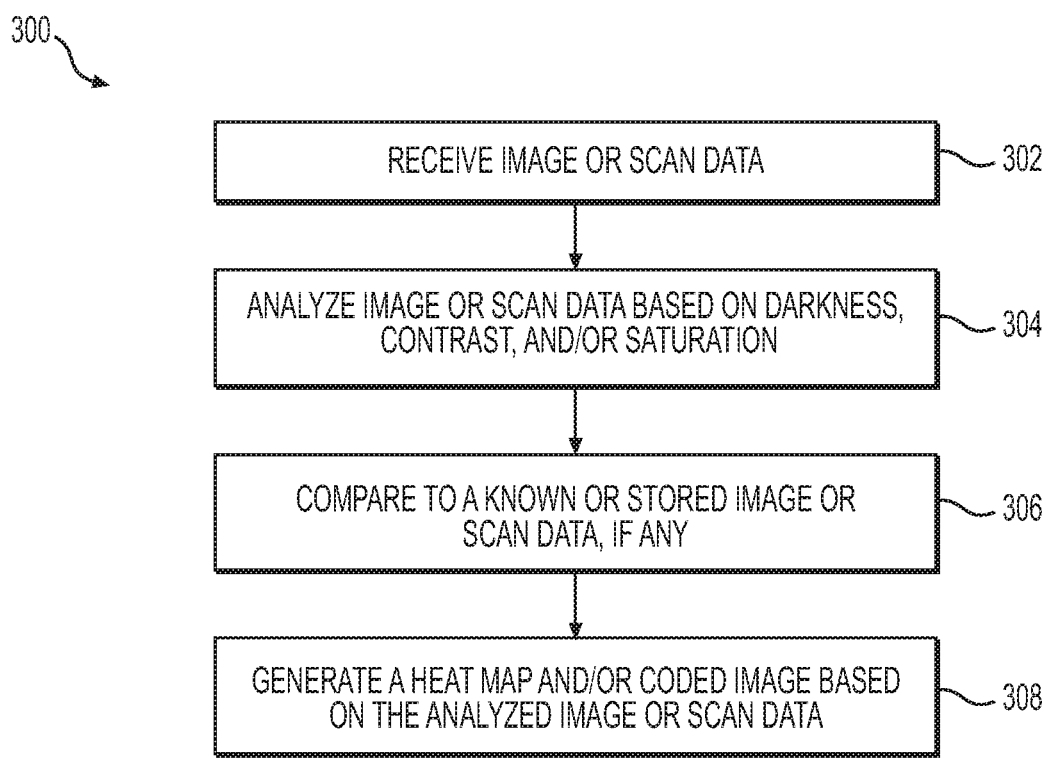
FIG. 3 is a flow diagram of an exemplary method for receiving, processing, and displaying images of a patient's organ and the organ's contents, according to aspects of the present disclosure.

FIG. 3 illustrates an exemplary method 300 for receiving, processing, and displaying images of a patient's organ and its contents, for example, a kidney and kidney stones, according to aspects of the present disclosure. In particular, the method 300 shown in FIG. 3 may help to ensure that a user properly identifies and then removes the entirety of the stone burden or other material.

In step 302, a processing unit, such as, for example, the processing unit within control unit 22 may receive image or scan data of the patient's organ obtained by imaging device 14. Then, in step 304, the processing unit may analyze the image or scan data based on the image or scan darkness, contrast, and/or saturation. The processing unit may analyze each pixel of the received image or scan data and compare each pixel to a scale, such as, for example, a grayscale. A portion of the values on the scale may correspond to a stone intensity, tissue intensity, bone intensity, and/or other known intensities, and the scale may be shifted or modified depending on whether a contrasting agent is used in step 202 above. The processing unit may also factor the intensity of the energy from imaging device 14 in the correspondence of the pixels to the particular scale. Based on the intensity of the pixels and their correspondence to the scale, the processing unit then determines the density, and thus the size, location, and/or burden, of the various detected elements. If the processing unit or memory unit contains any previously obtained or stored image or scan data of the patient's organ or a similar and/or ideal organ, the processing unit may compare the obtained image or scan data to the previously obtained or stored image or scan data in step 306, which may have been analyzed previously by the processing unit as discussed above.

Based on the aforementioned analysis, in step 308 the processing unit may produce or generate a heat map and/or coded image of the organ, which may be displayed on display 16. The heat map and/or coded image may be color coded, for example indicating material to be removed in red and areas free of material in green. Additionally, the heat map and/or coded image may include an outlined area that includes material to be removed, and the outlined area may also be color coded. For example, the outlined area may be based on a change in intensity or darkness of the pixels and/or a change in the determined density or tissue composition. In one aspect, if a patient's kidney is being scanned and analyzed, any stone burden may be indicated in red, and stone-free areas may be indicated in green. Alternatively, the coded image may include other colors, differing patterns, or indicia, such as, for example, circles, squares, triangles, or other shapes, to indicate material to be removed. In one aspect, materials having different sizes and/or densities may be indicated with different colors, patterns, surrounded by different shapes, etc. For instance, the coded image may indicate whether a stone may be removed with a particular retrieval device, or whether the stone is too large and requires lithotripsy. Similarly, the coded image may indicate an area, such as, for example, a kidney calyx, that is very likely to contain a stone, an area that is somewhat likely to contain a stone, an area that is likely free of stones, and an area that is definitely free of stones. The generated coded image may include a key to identify the various details and/or a scale to provide size and distance information to a user.

As a result, the user is able to refer to the heat map or coded image that identifies the material to be removed from the patient's organ. For example, if the organ is the patient's kidney, the user may be able to more easily determine the size, density, shape, and location of the kidney stones. The user may then plan which calyx or calyxes he or she should access with the delivery shaft 32 of medical device 12 to most effectively and efficiently remove the kidney stones. The user may also determine whether energy must be applied, for example, laser lithotripsy, to break up large kidney stones in order to be removed with a retrieval device. Additionally, the user may determine the parameters of the energy to apply.

Moreover, as shown in FIG. 2, the aforementioned image or scan analysis method 300 may be repeated during a medical procedure. In particular, the analysis method 300 shown in FIG. 3 may occur in steps 204 and 210 (as many times as necessary) of FIG. 2 in order to identify any material to be removed, as well as to ensure that the material to be removed has been fully removed.

Figure 4A:
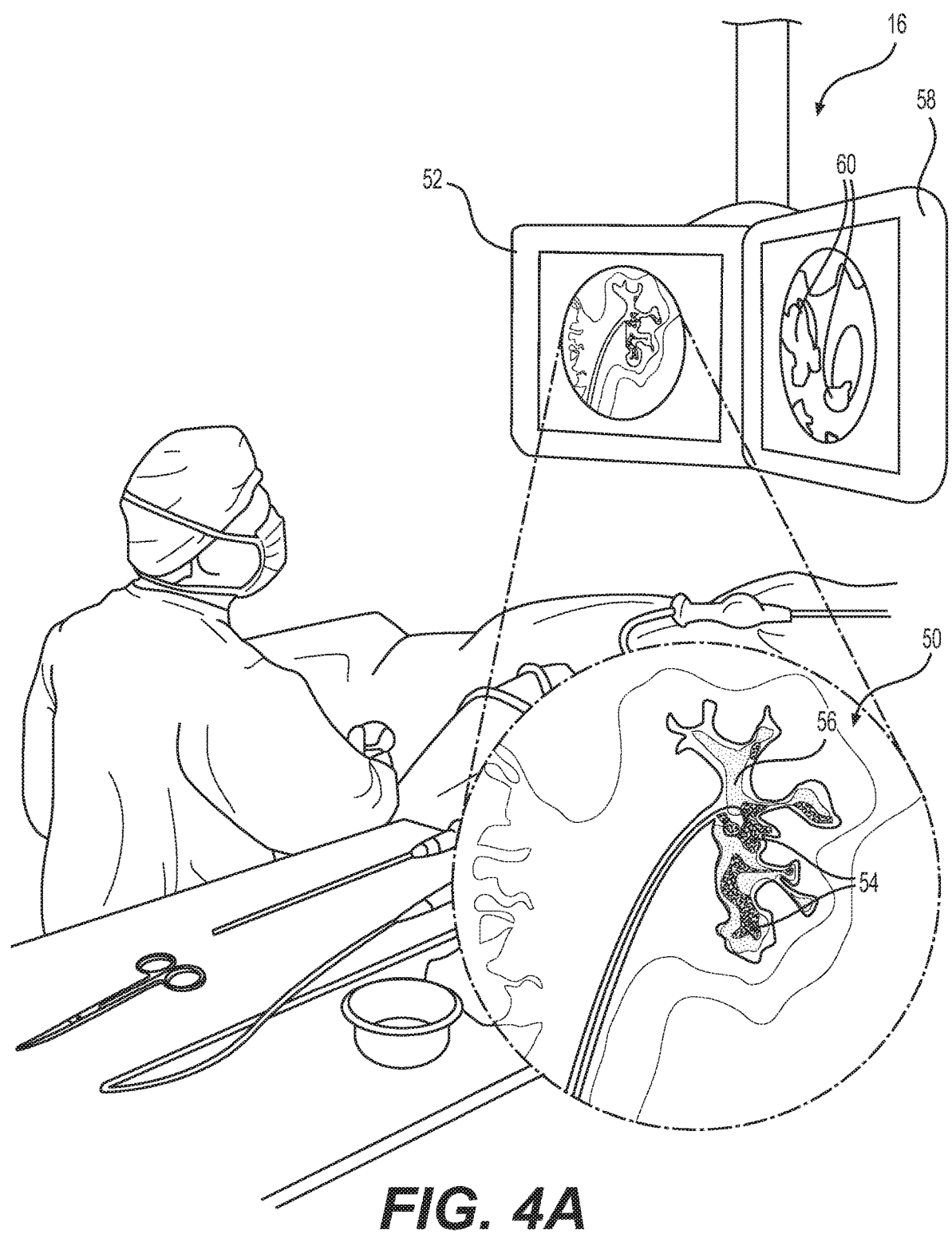
FIGS. 4A-4C illustrate images of a patient's kidney at different stages of kidney stone removal, according to aspects of the present disclosure.
Figure 4B:
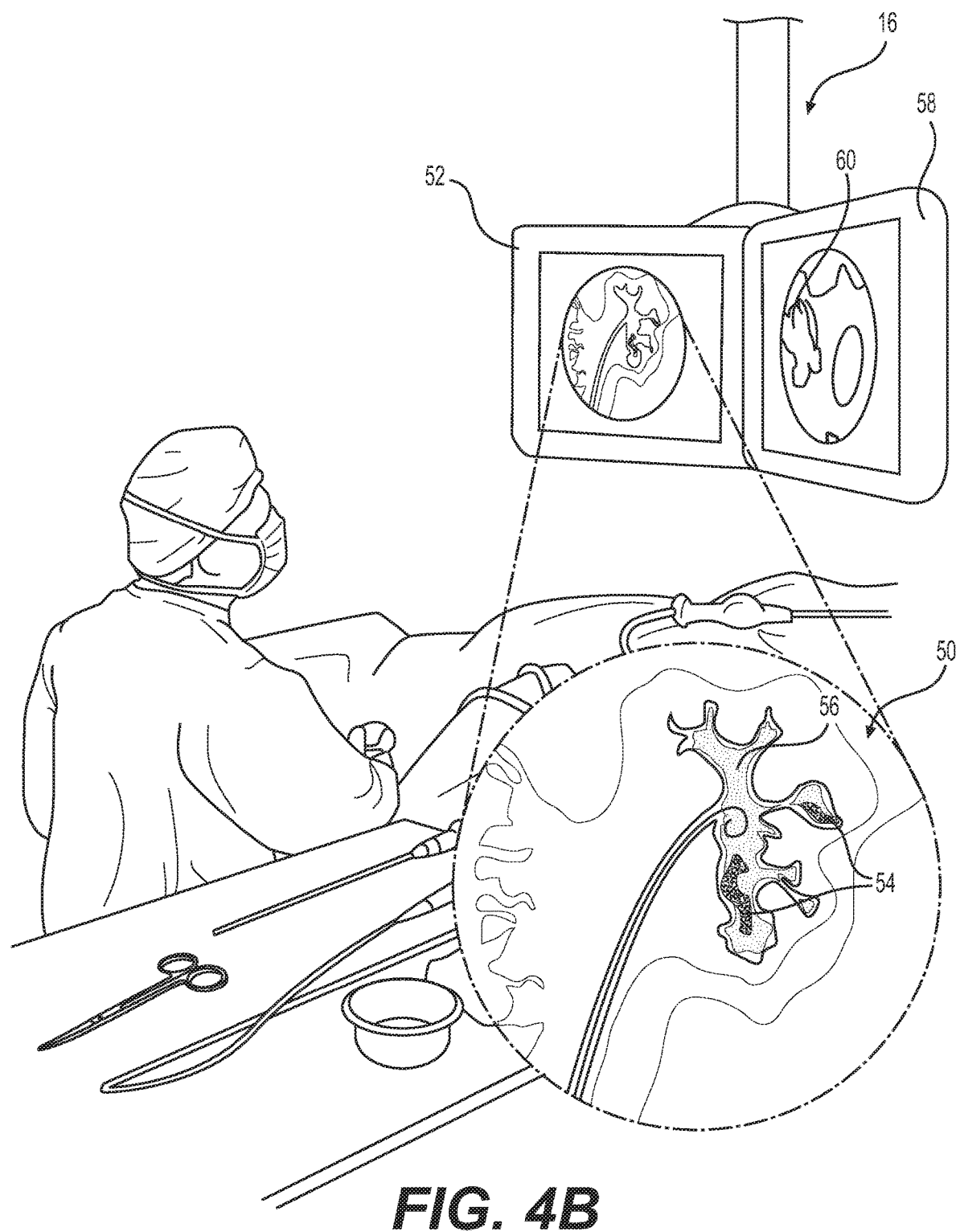
Figure 4C:
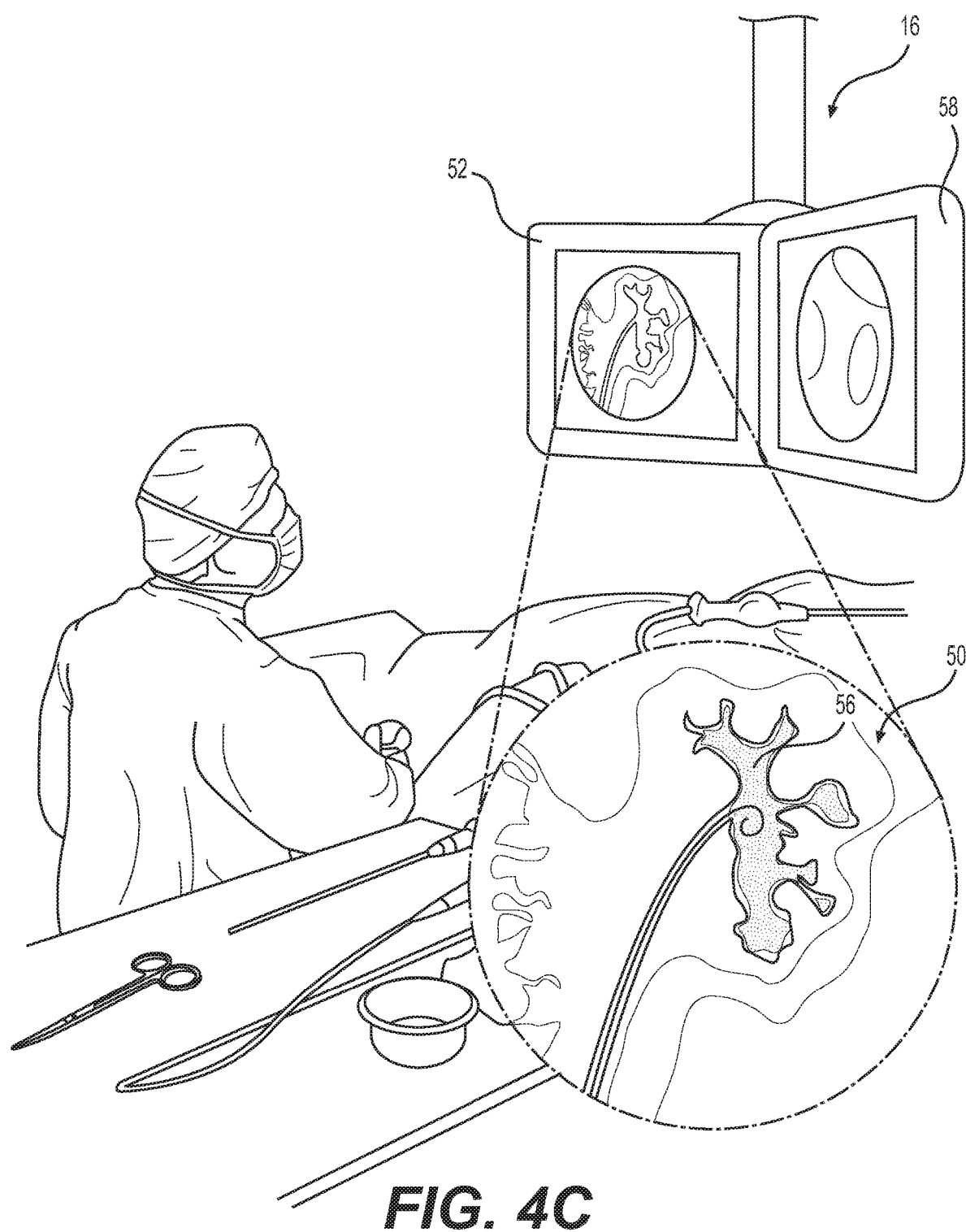

FIGS. 4A-4C illustrate exemplary images or scans that may be displayed to a user via display 16 at different stages of a material removal procedure to indicate a user's progress in material removal. FIG. 4A shows a user beginning a material removal procedure, such as, for example, ureteroscopic kidney stone removal from a patient's kidney 50. A first screen 52 of display 16 may display the coded image generated by the processing unit from images or scans obtained from imaging device 14, with the stone burden 54 shown in one pattern, and a stone-free area 56 shown in another pattern. It is noted that the stone burden 54 may also be shown in a color, such as, for example, red as discussed above, and the stone-free area 56 may be shown in green. The stone burden 54 or portions thereof may also be shown in different colors and/or patterns to indicate differing densities, sizes, materials, etc. A second screen 58 of display 16 may display images received by the camera located at the distal end of the delivery shaft 32 of medical device 12, which may allow the user to view the interior of kidney 50, including individual kidney stones 60. As discussed, the user may refer to the image displayed on screen 52 before and during the procedure to position the distal end of the delivery shaft 32 within the kidney 50. The user may apply energy to one or more kidney stones through one of the lumens within the delivery shaft 32, or may use a retrieval device to capture and/or remove the kidney stones.

FIG. 4B illustrates an intermediate stage of a material removal procedure. For example, the user may have removed several kidney stones from the kidney 50. However, the user may then be unsure whether the entirety of the kidney stone burden 54 has been removed. Therefore, the user may perform steps 208 and 210 of FIG. 2, and the processing unit may again perform method 300 of FIG. 3 to generate a new coded image from images or scans obtained from imaging device 14. It is noted that the medical device 12 may be positioned within the patient 20 during the imaging steps. During the performance of method 300, the processing unit may compare the obtained data to the data obtained before the procedure began, in particular, comparing the location, size, and density of the previously determined stone burden 54 to the potential stone burden in the new image or scan. Then, the new coded image may be displayed on the first screen 52. As shown, in this example, there are two areas within the kidney 50 where the stone burden 54 remains, with a larger stone-free area 56 than in FIG. 4A. As such, the user may then use the new coded image, as well as images of stone 60 from the camera at the distal end of the delivery shaft 32 on second screen 58, to continue the stone removal procedure.

FIG. 4C illustrates a final stage of a stone removal procedure where the patient's kidney 50 is free of stone burden 54. Again, the user may believe that he or she has removed all of the stone burden 54 from kidney 50. The user may perform steps 208 and 210 of FIG. 2, and the processing unit may again perform method 300 of FIG. 3 to generate a new coded image from images or scans obtained from imaging device 14. Then, if the user has indeed removed all of the stone burden 54, the new coded image displayed on first screen 52 will indicate the entirety of kidney 50 as a stone-free area 56. Additionally, as shown on second screen 58, the images obtained from the camera at the distal end of delivery shaft 32 would also be free of any stones 60.

It is noted that the elements and functions of control unit 22 may be incorporated into the medical device 12. Medical device 12 may be coupled to imaging device 14 and to the display 16. Medical device 12 may also include the discussed memory and processing units that perform the functions associated with the control unit 22, for example, in the handle 26 of medical device 12. Therefore, the medical device 12 may also include controls in order to interface with and control the imaging device 14 and display 16. Additionally, the medical device 12 may include the software or applications to analyze the obtained images or scans and produce the coded images identifying the material to be removed. Medical device 12 may be connected to an electronic medical record database to view and/or add to the patient's medical history.

The disclosed medical systems 10 and methods 200 and 300 may help enable efficient and effective procedures to breakup and/or remove material from a patient's organ. In particular, the user may easily view the generated heat map and/or coded image, with the heat map and/or coded image identifying and providing details to the user about the material to be removed, for instance, kidney stones within the patient's kidney. Therefore, in the kidney stone example, the user may more efficiently remove the kidney stones 60 from specific locations within the patient's kidney 50 without wasting time exploring the kidney 50 with the distal end of the delivery shaft 32. Similarly, during the procedure, the user need not guess or conduct further exploration to determine whether the patient's kidney is free of stones. Instead, the user may obtain another heat map or coded image, which identifies the kidney stones 60, if any, that the user still must remove. Additionally, both before and during the procedure, the user need not guess or struggle to read poor resolution, often grayscale or monochrome, images of the patient's organ, which may lead to the user missing a kidney stone. Instead, the disclosed systems and methods help remove the uncertainty and subjectivity, while also providing enhanced images to the user that clearly identify material to be removed from a patient's organ.

Moreover, while much of this disclosure is directed to ureteroscopic kidney stone removal, with or without lithotripsy, it is further contemplated that the systems and procedures discussed herein may be equally applicable to other material removal procedures. For example, the systems and methods discussed above may be used during a percutaneous nephrolithotomy/nephrolithotripsy (PCNL) to plan for a procedure and mid-procedure to locate any missed kidney stones. The systems and methods discussed above may also be used to plan for or conduct procedures to remove ureteral stones, gallstones, bile duct stones, etc. The methods and systems discussed above may further be used to plan for and/or conduct any procedure that relies upon monochrome imaging.

While principles of the present disclosure are described herein with reference to illustrative examples for particular applications, it should be understood that the disclosure is not limited thereto. Those having ordinary skill in the art and access to the teachings provided herein will recognize additional modifications, applications, embodiments, and substitution of equivalents all fall within the scope of the features described herein. Accordingly, the claimed features are not to be considered as limited by the foregoing description.

We claim:

1. A method for identifying material to be removed from a patient using an imaging device, a display, a control unit, and an insertion device, wherein the insertion device includes a deflectable delivery shaft and at least one camera positioned at a distal end of the delivery shaft, the method comprising:
    obtaining a first set of image data from the imaging device;
    sending the first set of image data to the control unit from the imaging device;
    analyzing the first set of image data based on at least one of a darkness, a contrast, or a saturation, and generating a coded image identifying the material to be removed from the patient to be displayed on the display;
    displaying the coded image on a first screen of the display;
    indicating the material to be removed with the insertion device based on the displayed coded image, wherein the coded image includes the size of the material and an indication of whether the material can be removed from the patient with a retrieval device extended through a lumen of the delivery shaft of the insertion device;
    displaying images obtained from the camera on a second screen of the display; and
    removing at least a portion of the material from the patient with the insertion device.

2. The method of claim 1, wherein removing at least the portion of the material from the patient includes:
    deflecting the delivery shaft of the insertion device; and
    illuminating an organ of the patient with a light source positioned at the distal end of the delivery shaft.

3. The method of claim 1, wherein the obtained image data is grayscale or monochrome, and the method further includes identifying the material to be removed from the patient with a different color, pattern, or shape than an area that is free of the material to be removed.

4. The method of claim 1, further including indicating the location of the material relative to an organ of the patient, identifying the material to be removed from the patient based on density, and indicating the size of the material and whether the material may be removed from the patient with a retrieval device.

5. The method of claim 1, wherein obtaining the first set of image data from the imaging device includes using a rotatable C-arm X-ray machine including an X-ray tube and an X-ray detector configured to be positioned on opposing sides of the patient; and
    wherein the control unit is integrally incorporated within a handle of the insertion device.

6. The method of claim 1, further including obtaining a second set of image data from the imaging device and comparing the second set of image data with the coded image generated based on the first set of image data.

7. The method of claim 6, further including, based on the comparison of the second set of image data with the generated coded image and the first set of image data, indicating progress of a material removal procedure.

8. A system for identifying material to be removed from a patient comprising:
    an imaging device configured to obtain image data;
    a display configured to display images;
    an insertion device; and
    a control unit,
    wherein the control unit is configured to receive a first set of image data from the imaging device, analyze the first set of image data based on at least one of a darkness, a contrast, or a saturation, and generate a coded image identifying the material to be removed from the patient to be displayed on the display,
    wherein the insertion device includes a deflectable delivery shaft having at least one lumen extending through the delivery shaft,
    wherein the delivery shaft includes at least one camera positioned at a distal end of the delivery shaft,
    wherein the display includes at least two screens, wherein a first screen displays the coded image and a second screen displays images from the camera, and
    wherein the coded image generated by the control unit includes the size of the material and an indication of whether the material can be removed from the patient with a retrieval device extended through a lumen of the delivery shaft of the insertion device.

9. The system of claim 8, wherein the delivery shaft includes a light source positioned at the distal end of the delivery shaft.

10. The system of claim 8, wherein the control unit includes a processing unit and a memory unit;
    wherein the control unit is configured to signal the imaging device to obtain a second set of image data; and
    wherein the control unit is further configured to compare the second set of image data with the coded image generated based on the first set of image data.

11. The system of claim 10, wherein based on the comparison of the second set of image data with the coded image generated based on the first set of image data, the control unit is further configured to indicate progress during a material removal procedure.

12. The system of claim 8, wherein the obtained image data is grayscale or monochrome, and wherein the control unit is configured to generate the coded image that identifies the material to be removed from the patient with a different color, pattern, or shape than an area that is free of the material to be removed.

13. The system of claim 8, wherein the material to be removed from the patient is one or more kidney stones in a kidney of the patient, and wherein the control unit is configured to:
    indicate the location of the one or more kidney stones relative to the kidney of the patient,
    identify the one or more kidney stones to be removed from the patient based on density, and
    indicate the size of the one or more kidney stones and whether the one or more kidney stones may be removed from the kidney of the patient with a retrieval device extended through the lumen of the of the delivery shaft.

14. The system of claim 8, wherein the imaging device is a rotatable C-arm X-ray machine including an X-ray tube and an X-ray detector configured to be positioned on opposing sides of the patient; and wherein the control unit is integrally incorporated within a handle of the insertion device.

15. The system of claim 8, wherein the first screen and the second screen are adjacent on the display.

16. A non-transitory computer-readable medium for identifying material to be removed from a kidney of a patient, comprising instructions stored thereon, that when executed on a processor, perform the steps of:
receiving a first set of image data, wherein the first set of image data is received from an imaging device;
analyzing the first set of image data based on at least one of a darkness, a contrast, or a saturation, and generating a coded image identifying the material to be removed from the patient displayable on a first screen of a display, wherein the step of generating the coded image includes indicating the size of the material and whether the material can be removed from the patient with a retrieval device extended through a lumen of a delivery shaft of an insertion device;
sending the coded image to the first screen of the display;
receiving images from a camera positioned on a distal end of the delivery shaft of the insertion device; and
displaying the images received from the camera on a second screen of the display.

17. The non-transitory computer-readable medium of claim 16, wherein the step of receiving images from the camera positioned on the distal end of the delivery shaft of the insertion device includes the distal end of the delivery shaft being positioned within the kidney of the patient, wherein the step of generating the coded image identifying the material to be removed from the patient includes indicating the location of the material relative to the kidney of the patient, identifying the material to be removed from the patient with a different color, pattern, or shape than an area that is free of the material to be removed, and indicating the density of the material.

18. The non-transitory computer-readable medium of claim 16, wherein the step of receiving the first set of image data includes receiving image data from a rotatable C-arm X-ray machine including an X-ray tube and an X-ray detector configured to be positioned on opposing sides of the patient; and
wherein the step of analyzing the first set of image data is performed by a processing unit integrally incorporated within a handle of the insertion device.

19. The non-transitory computer-readable medium of claim 16, further including the step of comparing a second set of image data with the coded image generated based on the first set of image data.

20. The non-transitory computer-readable medium of claim 19, further including the step of, based on the comparison of the second set of image data with the generated coded image and the first set of image data, indicating progress of a material removal procedure.

* * * * *